(12) United States Patent
Takinami (10) Patent No.: US 10,436,718 B2
(45) Date of Patent: Oct. 8, 2019

(54) COMPONENT MEASUREMENT APPARATUS AND MEASUREMENT CHIP

(71) Applicant: Terumo Kabushiki Kaisha, Tokyo (JP)

(72) Inventor: Masao Takinami, Asaka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 195 days.

(21) Appl. No.: 15/388,656

(22) Filed: Dec. 22, 2016

(65) Prior Publication Data

US 2017/0102336 A1     Apr. 13, 2017

Related U.S. Application Data

(63) Continuation of application No. PCT/JP2015/070538, filed on Jul. 17, 2015.

(30) Foreign Application Priority Data

Sep. 29, 2014 (JP) ................................ 2014-198091

(51) Int. Cl.
  *G01N 21/03*     (2006.01)
  *G01N 21/78*     (2006.01)
  (Continued)

(52) U.S. Cl.
  CPC ........ *G01N 21/78* (2013.01); *B01L 3/502715* (2013.01); *G01N 21/01* (2013.01);
  (Continued)

(58) Field of Classification Search
  CPC combination set(s) only.
  See application file for complete search history.

(56) References Cited

U.S. PATENT DOCUMENTS 3,954,341 A * 5/1976 Uffenheimer .......... G01N 21/05
                                                                  356/410
4,088,448 A   5/1978 Lilja et al.
                        (Continued)

FOREIGN PATENT DOCUMENTS

EP     2098161 A1    9/2009
JP     2505710       6/1996
              (Continued)

OTHER PUBLICATIONS

International Search Report (with English translation) for International (PCT) Patent Application No. PCT/JP2015/070538, dated Oct. 13, 2015, 3 page.

(Continued)

*Primary Examiner* — Paul S Hyun
(74) *Attorney, Agent, or Firm* — Jason H. Vick; Sheridan Ross, PC (57) ABSTRACT

A blood glucose meter (component measurement apparatus) includes a measurement chip, and an apparatus main body including an insertion hole. The measurement chip includes a pair of plate pieces, a spacer arranged between the pair of plate pieces, and a cavity that can retain blood. A pair of wall portions of the insertion hole, facing each other at a measurement unit and in the vicinity of the measurement unit, is separated from each other with a width smaller than a thickness of the measurement chip in a lamination direction. The spacer elastically deforms by a state in which the pair of plate pieces is pressed by the pair of wall portions and defines a width of the cavity.

20 Claims, 6 Drawing Sheets

(51) Int. Cl.
*G01N 21/01* (2006.01)
*G01N 33/52* (2006.01)
*B01L 3/00* (2006.01)
*G01N 21/84* (2006.01)
*G01N 21/05* (2006.01)
*G01N 21/77* (2006.01)
*G01N 35/00* (2006.01)

(52) U.S. Cl.
CPC ......... *G01N 21/03* (2013.01); *G01N 21/8483* (2013.01); *G01N 33/526* (2013.01); *B01L 2300/0654* (2013.01); *B01L 2300/0825* (2013.01); *B01L 2300/123* (2013.01); *B01L 2400/0406* (2013.01); *G01N 2021/0325* (2013.01); *G01N 2021/0346* (2013.01); *G01N 2021/0364* (2013.01); *G01N 2021/056* (2013.01); *G01N 2021/7766* (2013.01); *G01N 2035/00108* (2013.01)

(56) References Cited

U.S. PATENT DOCUMENTS

| | | | |
|---|---|---|---|
| 4,575,038 A * | 3/1986 | Moore | H05K 7/12 248/316.7 |
| 4,675,019 A | 6/1987 | Bellhouse et al. | |
| 5,424,035 A | 6/1995 | Hones et al. | |
| 5,570,447 A * | 10/1996 | Liu | G01N 21/0303 385/125 |
| 6,618,137 B1 | 9/2003 | Sawa et al. | |
| 2012/0135446 A1 * | 5/2012 | Collins | B01L 3/502776 435/29 |
| 2013/0333453 A1 | 12/2013 | Platte et al. | |
| 2015/0260693 A1 * | 9/2015 | DeMarco | G01N 30/26 356/72 |

FOREIGN PATENT DOCUMENTS

| | | |
|---|---|---|
| JP | 2001-147190 | 5/2001 |
| JP | 2005-121414 | 5/2005 |
| JP | 2007-278885 | 10/2007 |
| JP | 2008-082898 | 4/2008 |
| JP | 2012-127904 A | 7/2012 |
| JP | 2013-148521 A | 8/2013 |

OTHER PUBLICATIONS

Kameya, Yuki et al. "Enhancement of Solar Radiation Absorption Using Nanoparticle Suspension" Science Direct; Solar Energy vol. 85, No, 2; pp. 299-307; Feb. 1, 2011.

European Search Report for corresponding European Patent Application No. 15847573.1, dated Apr. 19, 2018.

International Preliminary Report on Patentability (with English translation) for International (PCT) Patent Application No. PCT/JP2015/070538, dated Apr. 4, 2017, 8 pages.

Official Action (with English translation) for Chinese Patent Application No. 201580019881.4, dated Jun. 16, 2017, 7 pages.

* cited by examiner

COMPONENT MEASUREMENT APPARATUS AND MEASUREMENT CHIP

CROSS REFERENCE TO RELATED APPLICATIONS

This Application is a continuation of and claims priority to PCT/JP2015/070538, filed on Jul. 17, 2015, entitled "COMPONENT MEASUREMENT DEVICE AND MEASUREMENT CHIP", which claims priority to Japanese Application No. 2014-198091 filed Sep. 29, 2014, entitled "COMPONENT MEASUREMENT DEVICE AND MEASUREMENT CHIP", each of which are incorporated herein by reference in their entirety for all that it teaches and for all purposes.

TECHNICAL FIELD

The present invention relates to a component measurement apparatus and a measurement chip for measuring a component of a liquid.

BACKGROUND

There is a known component measurement apparatus (blood glucose meter) for measuring glucose in blood (liquid) to diagnose diabetes and to determine insulin dosage. Measurement principles of this type of blood glucose meter include an "electrode-system" and a "colorimetric-system". In the electrode-system, reagent is applied around the electrode and an electrical change at introduction of blood is measured. In the colorimetric-system, blood that flows or stays is reacted with the reagent and the color-developing degree is optically measured.

A blood glucose meter employing the colorimetric-system is configured, for example, such that a measurement chip for blood sampling is attached to an apparatus main body, a measurement unit emits measurement light with a predetermined wavelength toward the color-developed blood within the measurement chip, and receives reflection light, thereby calculating and displaying component quantity and characteristics (refer to Japanese Patent Application No. JP 2505710 B, which is incorporated herein by reference in its entirety for all that it teaches and for all purposes, or the like). In this case, to stabilize accuracy in every measurement, it is important that a blood glucose meter constantly achieves, at measurement, a fixed distance between the measurement unit and the measurement chip. The component measurement apparatus disclosed in Japanese Patent Application No. JP 2505710 B is configured such that, a measurement chip is pressed by a stationary pressing element of the apparatus main body, in a state where the measurement chip is attached to the apparatus, thereby maintaining a distance between a test field (liquid holding unit on the measurement chip) and the measurement unit.

SUMMARY

Meanwhile, the measurement unit of the colorimetric-system blood glucose meter (component measurement apparatus) may be configured to arrange a measurement chip between a light emitting unit and a light receiving unit and to allow the measurement light emitted from the light emitting unit to be transmitted through the measurement chip to be received at the light receiving unit. In the configuration to allow the measurement light to be transmitted through the measurement chip, it would be important, to enhance measurement accuracy, to manufacture the measurement chip with high dimensional accuracy, specifically, to manufacture the tip that constantly achieves not only a fixed distance between the measurement chip and the measurement unit, but also a fixed thickness of the measurement chip through which the measurement light is transmitted.

The measurement chip, however, is discarded after one-time use for measurement and thus is mass-produced. Therefore, when the manufacture of the measurement chips includes mass-production involving molding with high dimensional accuracy, this might lead to inconvenience of significantly increasing labor and cost for the manufacture.

The embodiments herein are made in view of the above-described issue(s) and intended to provide a component measurement apparatus and a measurement chip, that enable easy manufacture of the measurement chip at low cost and component measurement with high accuracy and stability.

To achieve the above-described intention, the embodiments herein are a component measurement apparatus that includes a measurement chip, and an apparatus main body having an insertion hole, and that is configured to measure a component of a liquid taken into the measurement chip in a state where the measurement chip is inserted in the insertion hole, by a measurement unit inside the insertion hole. The measurement chip includes a set of plate pieces that has hardness and is arranged in a lamination direction, a spacer arranged between the set of plate pieces, and a liquid-retainable cavity that is enclosed by the set of plate pieces and the spacer and capable of retaining the liquid. In this configuration, at least a pair of wall portions facing each other at the measurement unit and in the vicinity of the measurement unit, among the wall portions constituting the insertion hole, is separated from each other with a width smaller than a thickness of the measurement chip in the lamination direction, formed by the set of plate pieces and the spacer. The spacer elastically deforms with a state in which the set of plate pieces is pressed by the pair of wall portions at the measurement unit and in the vicinity of the measurement unit, in an insertion state into the insertion hole, and defines a width of the liquid-retainable cavity.

According to the above-described configuration, the component measurement apparatus is configured such that the set of plate pieces is pressed by the pair of wall portions on the insertion hole and the elastically deformed spacer defines the width of the set of plate pieces, thereby constantly achieving a fixed level of thickness (cell length) of a measurement target portion that retains liquid and is used for measurement, of the measurement chip. With this configuration, even when the cell length includes an error in a non-insertion state at the insertion hole, the cell length of the measurement chip is favorably changed to a cell length defined in an insertion state into the insertion hole, making it possible to perform component measurement of a liquid with high accuracy and stability. Moreover, it is possible to easily perform mass-production without the need to pay too much attention to the dimensional accuracy of the measurement chip, and thus, to achieve the manufacture with low cost and less labor of manufacture.

In this case, the pair of wall portions can be formed with a material harder than the set of plate pieces. The material of the wall portion would be a material that is hard, unlikely to be easily changed in dimensions, unlikely to be easily worn after repetitive insertion/removal of the measurement chip, and can be processed with high dimensional accuracy. Example of the materials include metal such as stainless steel and titanium, alumite coating-processed aluminum, liquid crystal polymer, plastic to which filler including glass and mica is added, plastic having a surface cured coated with nickel-plating, etc., carbon fiber, and fine ceramics.

By forming the pair of wall portions with a hard material in this manner, it is possible to firmly maintain the shape of the insertion hole, reduce the measurement chip inserted into the insertion hole, and define the thickness in the lamination direction with high accuracy.

More specifically, the pair of wall portions may be formed with a hard metallic material.

By forming the pair of wall portions with hard metallic material in this manner, it is possible to easily mold the insertion hole with high dimensional accuracy in the manufacture (injection molding, press molding, or the like).

The spacer may be formed in a pair, sandwiching the liquid-retainable cavity therebetween.

By providing the spacer in pair, sandwiching the liquid-retainable cavity therebetween in this manner, the pair of spacers can be elastically and integrally deformed, making it possible to uniformly decrease the cell length of the measurement target portion. This makes it possible to further enhance component measurement accuracy.

Still further, the measurement chip may be configured such that the thickness in the lamination direction is set to a range of 101% to 105% with respect to the width of the pair of wall portions, in a state where the tip is in a non-insertion state at the insertion hole.

In this manner, when the thickness of the measurement chip in the lamination direction is set to a range of 101% to 105% with respect to the width of the pair of wall portions, it is possible to reliably reduce the thickness of the measurement chip by pressing the measurement chip in a state where the tip is inserted into the insertion hole, namely possible to constantly achieve a uniform thickness. Moreover, with the elastic deformation of the spacer, it is possible to prevent the liquid-retainable cavity from being significantly narrowed inwardly, and thus, to further enhance the component measurement accuracy.

Furthermore, to achieve the above-described intention, the embodiments are a measurement chip configured to be inserted into an insertion hole of an apparatus main body of a component measurement apparatus and allow a component of a liquid that has been taken in, to be measured by a measurement unit inside the insertion hole. The measurement chip includes a set of plate pieces that has hardness and is arranged in a lamination direction, a spacer arranged between the set of plate pieces, and a liquid-retainable cavity that is enclosed by the set of plates and the spacer and capable of retaining the liquid. The spacer elastically deforms with a state in which the set of plate pieces is pressed by a pair of wall portions constituting the insertion hole at the measurement unit and in the vicinity of the measurement unit, in an insertion state into the insertion hole, and defines a width of the liquid-retainable cavity.

The component measurement apparatus and the measurement chip enable easy manufacture of the measurement chip at low cost and enable component measurement with high accuracy and stability.

DETAILED DESCRIPTION

Hereinafter, a component measurement apparatus and a measurement chip will now be described in detail with reference to embodiments and attached drawings.

Figure 1:
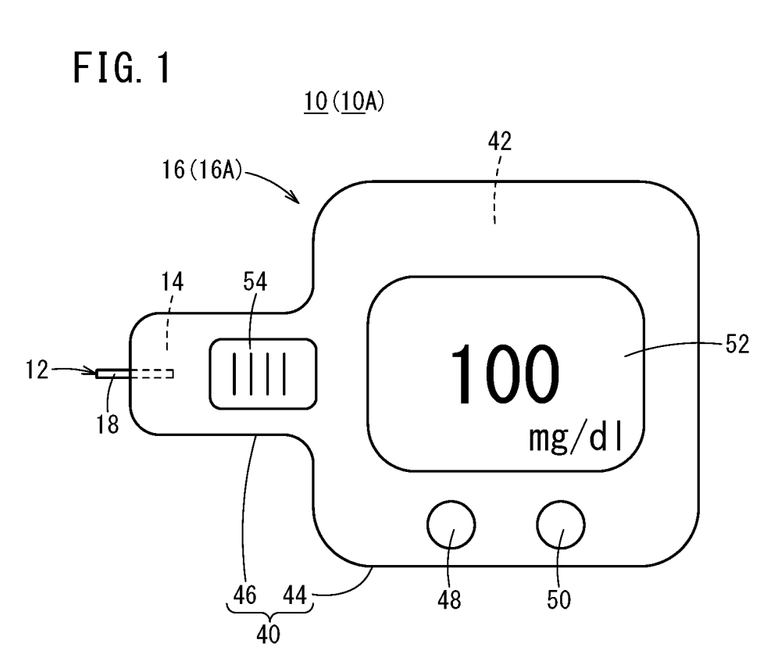
FIG. 1 is a plan view schematically illustrating an embodiment of a blood glucose meter (component measurement apparatus).

A component measurement apparatus 10 is formed, as illustrated in FIG. 1, as an apparatus for measuring glucose (component) in blood (liquid), namely, as a blood glucose meter (accordingly, hereinafter, the apparatus will also be referred to simply as a blood glucose meter 10). The blood glucose meter 10 is mainly applied for personal use, operated by a user (patient). The user measures blood glucose before meal and manages one's own blood glucose. Of course, medical workers can also use the blood glucose meter 10 to measure the blood glucose of the patient and, in this case, the blood glucose meter 10 may be appropriately modified to be able to be installed at a medical facility, or the like.

The blood glucose meter 10 employs a colorimetric-system blood glucose measurement principle, in which a component quantity of glucose in blood (blood glucose level) is optically measured. In particular, the blood glucose meter 10 performs blood glucose measurement using a transmission-type measurement unit 14 (also refer to FIG. 2) configured to emit measurement light of a predetermined wavelength to blood and receive the light transmitted through the blood.

Hereinafter, specific configurations of the blood glucose meter 10 will be described. The blood glucose meter 10 includes a measurement chip 12 and an apparatus main body 16. While the measurement chip 12 is attached onto the apparatus main body 16, the blood glucose meter 10 takes in blood onto the measurement chip 12, and measures blood glucose by the measurement unit 14 of the apparatus main body 16. The measurement chip 12 is disposal type that is discarded every time after one-time use for measurement. In contrast, the apparatus main body 16 is a portable and robust apparatus so as to be repeatably used for blood glucose measurement easily by the user.

A portion of the measurement chip 12 of the blood glucose meter 10 protrudes to the outside of the apparatus main body 16 with the tip being attached onto the apparatus main body 16. Blood glucose measurement inside the apparatus main body 16 is enabled when blood is taken into the measurement chip 12 from the protruding portion. Specifically, the measurement chip 12 includes a tip main body portion 18 and a cavity 20 (liquid-retainable cavity). The tip main body portion 18 has a plate shape. The cavity 20 extends in a surface direction of a plate surface inside the tip main body portion 18.

Figure 2:
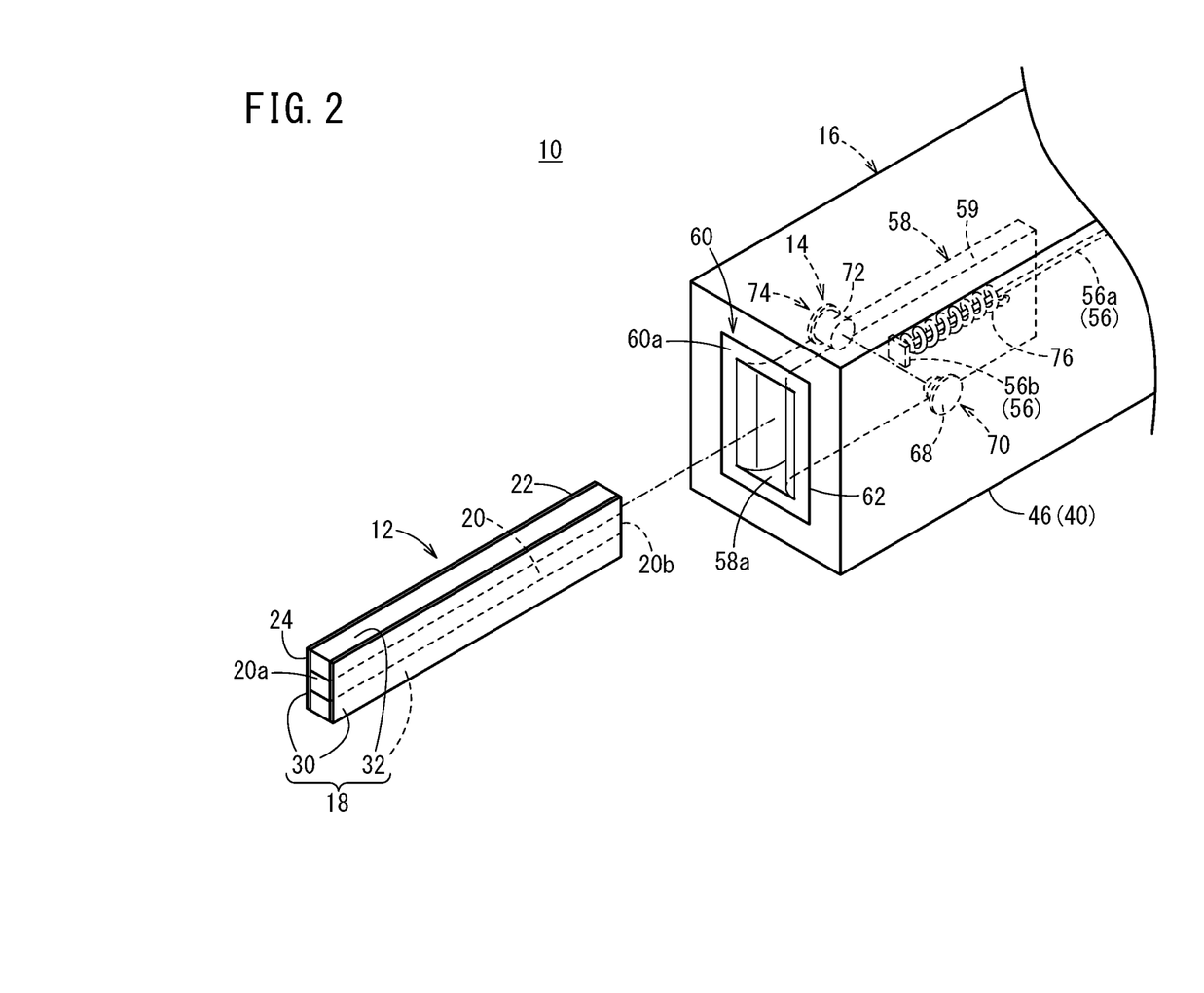
FIG. 2 is a perspective view illustrating enlarged figures of a measurement chip and a photometric block of an apparatus main body, illustrated in FIG. 1.
Figure 3A:
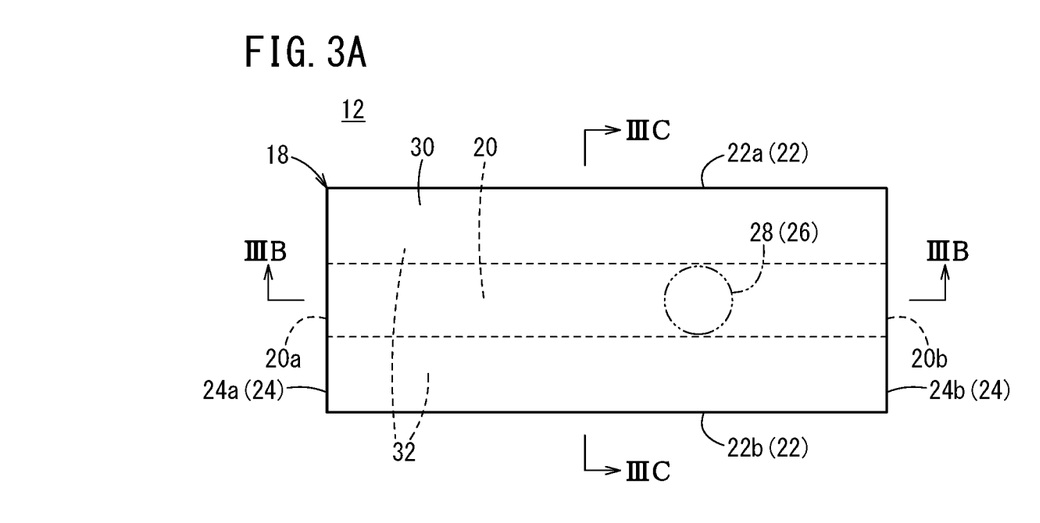
FIG. 3A is a side view illustrating the measurement chip in FIG. 1.
Figure 3B:
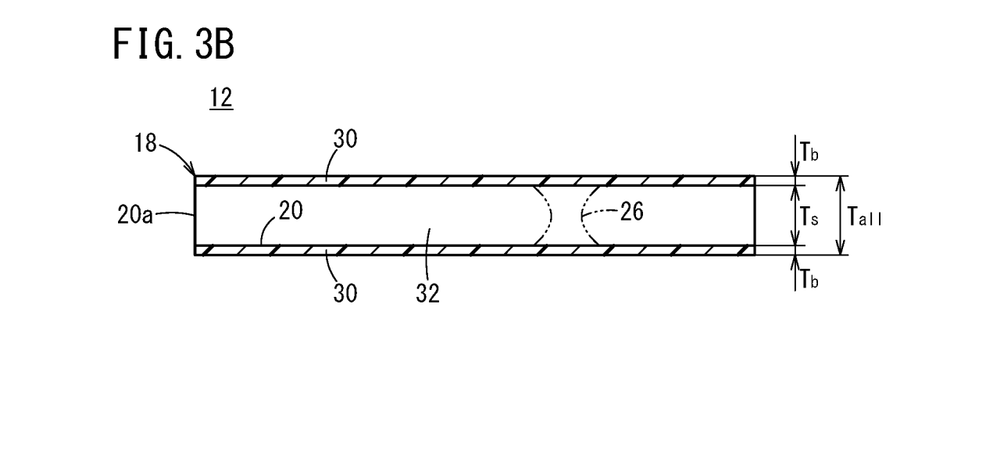
FIG. 3B is a cross-sectional view of FIG. 3A, taken along line IIIB-IIIB.
Figure 3C:
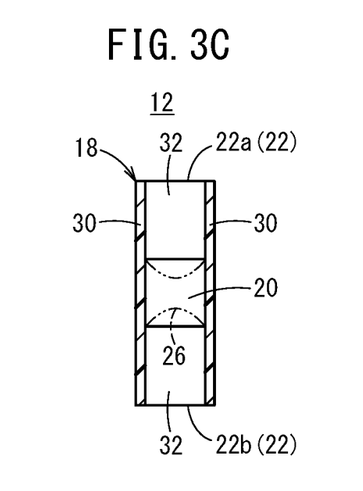
FIG. 3C is a cross-sectional view of FIG. 3A, taken along line IIIC-IIIC.

As illustrated in FIGS. 2 and 3A, the tip main body portion 18 has a rectangular shape, with a long side 22 elongated in the insertion and removal directions of the apparatus main body 16 (distal end and proximal end directions of the apparatus main body 16) in a side view, and a short side 24 (distal end side 24a and proximal side 24b) shortened in the up-down directions. For example, the length of the long side 22 of the tip main body portion 18 may be set to a length twice the length of the short side 24, or more. With this setting, the measurement chip 12 can ensure a sufficient insertion amount with respect to the apparatus main body 16.

Additionally, the thickness of the tip main body portion 18 is configured to be extremely small (thin) compared with the side surface formed in a rectangular shape (diagrams in FIGS. 2 to 5 are illustrated such that there is a sufficient thickness to facilitate understanding of the embodiments). For example, the thickness of the tip main body portion 18 may be set to one-tenth of the above-described short side 24, or less. The thickness of the tip main body portion 18 may appropriately be designed according to the shape of an insertion hole 58 of the apparatus main body 16. The configuration of this will be described below.

While the size of the tip main body portion 18 is not particularly limited, for example, the design ranges may be approximately 10 mm to 30 mm for the long side 22, approximately 5 mm to 15 mm for the short side 24, and approximately 0.05 mm to 0.5 mm for the thickness. With these size ranges, the measurement chip 12 can be easily treated by the user, and since the measurement chip 12 is sufficiently small, it is possible to suppress the material cost.

Note that although the corner portions of the tip main body portion 18 are sharp in FIG. 3A, the corners may be rounded, for example. Additionally, the shape of the tip main body portion 18 is not limited to the thin plate shape, but may be freely designed, of course. For example, the tip main body portion 18 may be formed in a square, other polygons, a circle (including ellipse), or the like, in a side view.

The cavity 20 provided inside the tip main body portion 18 is located at an intermediate position of the tip main body portion 18 in the up-down direction, formed in a straight line across the longitudinal direction of the tip main body portion 18. The cavity 20 is connected to a distal end port 20a formed at a distal end side 24a of the tip main body portion 18 and a proximal end port 20b formed at a proximal end side 24b of the tip main body portion 18, and communicates with the outside of the tip main body portion 18. The cavity 20 takes in the blood of the user from the distal end port 20a, and can allow the blood to flow along the extending direction on the basis of capillary action. The amount of blood that flows in the cavity 20 is small, and thus, even when the blood moves to the proximal end port 20b, leaking is suppressed by tension. Note that an absorption portion to absorb blood (for example, a spacer 32 formed with a porous material solely on the proximal end side) may be provided on the side of the proximal end side 24b of the tip main body portion 18.

Additionally, a reagent 26 for developing color on blood is applied to a predetermined position of the cavity 20 (for example, a position slightly close to the proximal end, from the intermediate point between the distal end port 20a and the proximal end port 20b, illustrated in FIG. 3A) and also a measurement target portion 28 to be measured by the apparatus main body 16 is set onto this predetermined position. The blood that flows inside the cavity 20 in the proximal end direction develops color by reacting with the applied reagent 26. Note that in the upper portion of the cavity 20 in the longitudinal direction, the application position of the reagent 26 and the measurement target portion 28 may be shifted with each other. For example, the reagent 26 may be applied on the upstream side in the blood flow direction of the measurement target portion 28.

The measurement chip 12 is configured such that the tip main body portion 18 includes a pair of plate pieces 30 and a pair of spacers 32 so as to form the above-described cavity 20. Each of the pair of plate pieces 30 has the above-described rectangular shape in a side view, being mutually arranged in the lamination direction. In short, the pair of plate pieces 30 forms both side surfaces (left and right side surfaces) of the tip main body portion 18. Plate thickness of each of the plate pieces 30 may be set to a very small size, for example, approximately 5 µm to 50 µm, being equal to each other. The thicknesses of the two (one set of) plate pieces 30 may be different from each other.

The pair of plate pieces 30 has a strength that would maintain a plate-shape and would not allow plastic deformation even when a certain degree of pressing force is applied from a direction orthogonal to the surface direction. Moreover, each of the plate pieces 30 is configured to be transparent or translucent so as to be able to transmit the measurement light. Furthermore, each of the plate pieces 30 may be configured to be a flat plate surface with an appropriate level of hydrophilicity so as to allow the blood to flow inside the cavity 20 (or coating agent may be applied to the plate surface).

While the material to form each of the plate pieces 30 is not particularly limited, it would be preferable to employ thermoplastic resin materials that can provide high molding accuracy with heating. Examples of thermoplastic resin material include polymeric materials such as polyethylene (including one formed as cyclic polyolefin), polypropylene, polyethylene terephthalate, polyvinyl chloride, polystyrene, ABS resin, acrylic, polyamide, polyester, fluororesin, or mixture of these. In particular, acrylic (including PMMA) is effective because it has high transparency and impact resistance. It would be, of course, possible to employ various materials such as glass and quartz other than the thermoplastic resin materials.

Additionally, the pair of spacers 32 is arranged to be sandwiched between the pair of plate pieces 30 and firmly bonded to a facing surface of each of the plate pieces 30 by a predetermined joining means (adhesive, or the like). In short, each of the spacers 32 is a member to form the cavity 20 between the pair of plate pieces 30 and the pair of spacers 32 themselves, by being arranged between the pair of plate pieces 30 so as to separate the pair of plate pieces 30 from each other. In this case, the one spacer 32 is arranged to come in contact with an upper long side 22a of the tip main body portion 18 in FIG. 3A and to extend in the distal end and proximal end directions along the upper long side 22a. The other spacer 32 is arranged to come in contact with a lower long side 22b of the tip main body portion 18 in FIG. 3B and to extend in the distal end and proximal end directions along the lower long side 22b.

In a side view, each of the pair of spacers 32 is formed in a rectangular shape having a long side that is the same size as the long side of the plate piece 30 and having a short side that is shorter than the shorter side of the plate piece 30 by about two-fifth to one-fifth. Additionally, a thickness $T_s$ of each of the spacers 32 may be designed to have appropriate dimensions according to a plate thickness $T_b$ of each of the pair of plate pieces 30 and according to the width of the insertion hole 58 of the apparatus main body 16, to be described below. These dimensions will be described below.

The pair of spacers 32 can be formed to be elastically deformable in mutually proximal directions of the pair of plate pieces 30 (inwardly in the lamination direction of the measurement chip 12). In short, with each of the plate pieces 30 being firmly sandwiched from an external side (power being applied in the lamination direction), the measurement chip 12 causes each of the spacers 32 to be elastically reduced, and changes the width of the pair of plate pieces 30 and the spacers 32, in the lamination direction.

Materials for forming the pair of spacers 32 are not particularly limited but examples of these may include various types of thermoplastic elastomer such as styrene series, polyolefin series, polyurethane series, polyester series, polyamide series, polybutadiene series, trans-polyisoprene series, fluoro-rubber series, and chlorinated polyethylene series. Alternatively, it is allowable to employ various elastically deformable materials other than thermoplastic elastomer, and to employ constructs such as elastically deformable porous materials (e.g. sponge). Moreover, it is allowable to employ, as the spacer 32, adhesive that joins the plate pieces 30 with each other, by being turned into a cured state or a semi-cured state between the pair of plate pieces 30. Still further, the spacer 32 may be configured to contain the reagent 26 and elute the reagent 26 into the cavity 20 with the pressing.

The measurement chip 12 is fundamentally configured as above. Next, the apparatus main body 16 of the blood glucose meter 10 will be described. As illustrated in FIG. 1, the apparatus main body 16 includes a housing 40 that represents an external view of the apparatus main body 16. The housing 40 includes a box portion 44 and a photometric block 46. The box portion 44 is formed in a size easily grasped and operated by the user, and contains therein a control unit 42 of the blood glucose meter 10. The photometric block 46 has a cylindrical shape, protrudes from a side (distal end side) of the box portion 44 in the distal end direction, and contains therein the measurement unit 14 that is an optical system. A power button 48, an operation button 50, and a display 52 are provided on an upper surface of the box portion 44. An eject lever 54 is provided on an upper surface of the photometric block 46.

The power button 48 switches start and stop of the blood glucose meter 10 according to user operation. The operation button 50 functions as an operation unit that, on the basis of the user operation, performs measurement and display of a blood glucose level, switches display of measurement results (including past blood glucose level), or the like, on the blood glucose meter 10 after being started. The display 52 is formed with liquid crystal, organic EL, or the like, and displays information to be supplied to the user in measurement of blood glucose levels, such as display of blood glucose levels and display or errors.

The eject lever 54 is movably provided in the distal end and proximal end directions, and configured to act on a locking mechanism (not illustrated) of an eject pin 56 (refer to FIG. 2) provided inside the photometric block 46. Specifically, the eject lever 54 is operated by the user in the distal end direction, thereby releasing the lock in the locking mechanism that fixes the eject pin 56 and enabling move of the eject pin 56 in the distal end direction.

Meanwhile, the photometric block 46 of the apparatus main body 16 is elongated to extend from the box portion 44 in the distal end direction so as to press the distal end to the user's finger, or the like. As illustrated in FIG. 2, the photometric block 46 includes a tip mounting portion 60 and the measurement unit 14. The tip mounting portion 60 includes the insertion hole 58. The measurement unit 14 optically detects glucose in the blood (blood glucose).

The tip mounting portion 60 includes, at its the distal end side, a flange portion 60a that is formed of a material (e.g. stainless steel) with high hardness (rigidity) and that protrudes in the outer direction. The tip mounting portion 60 has a cylindrical shape including a predetermined length in the axial direction. The tip mounting portion 60 is positioned and fixed across a distal end surface and an axis center portion (central portion) of the photometric block 46 formed with resin material. A fixing wall 46a that firmly fixes the tip mounting portion 60 is protrudingly formed at an inner surface of the photometric block 46.

The material of the tip mounting portion 60 would be a material that is hard, unlikely to be easily changed in dimensions, unlikely to be easily worn after repetitive insertion/removal of the measurement chip, and can be processed with high dimensional accuracy. Example of the materials include metal such as stainless steel and titanium, alumite coating-processes aluminum, liquid crystal polymer, plastic to which filler including glass and mica is added, plastic having a surface cured coated with nickel-plating, etc., carbon fiber, and fine ceramics. Among these, by employing metallic materials, it is possible to easily mold the insertion hole 58 with high dimensional accuracy in the manufacture (injection molding, press molding, or the like) of the tip mounting portion 60. The apparatus main body 16 may be configured to be integrally formed with the tip mounting portion 60 by forming the photometric block 46 itself of a hard material (for example, metallic materials).

At the axis center portion of the tip mounting portion 60, the insertion hole 58 is provided by being enclosed by a wall portion 62 of the tip mounting portion 60. The insertion hole 58 has a cross-sectional rectangular shape that is long in the up-down direction and short in the left-right width direction. The insertion hole 58 has a predetermined depth across a portion from the distal end surface toward the inner portion (proximal end direction) in a state where the tip mounting portion 60 is fixed onto the photometric block 46.

Figure 4A:
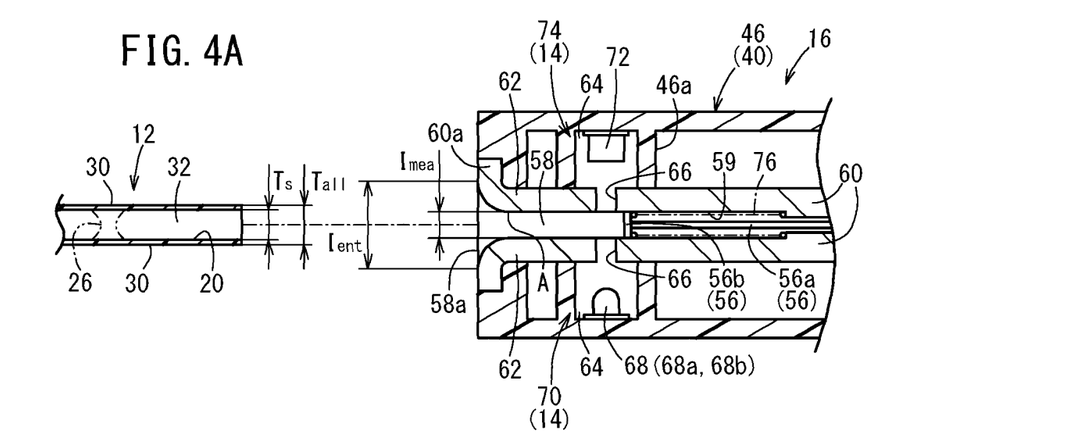
FIG. 4A is a first cross-sectional plan view illustrating attachment operation of the measurement chip with the apparatus main body, illustrated in FIG. 1.

An insertion opening portion 58a is provided at the distal end side of the tip mounting portion 60. The insertion opening portion 58a is connected to the insertion hole 58 and communicates with the outside. The dimension of the insertion opening portion 58a in the up-down direction corresponds to the dimension (length in the up-down direction) of the short side 24 of the measurement chip 12. Meanwhile, the dimension of the insertion opening portion 58a in the left-right width direction, namely, an interval $I_{ent}$ of a pair of wall portions 62 constituting a side surface of the insertion hole 58 is formed to be wider than a thickness $T_{all}$ of the measurement chip 12 in the lamination direction, as illustrated in FIG. 4A.

Moreover, the width of the pair of wall portions 62 becomes gradually small along a way from the insertion opening portion 58a toward the inner portion of the photometric block 46. Specifically, each of the wall portions 62 is formed into a curved surface that is curved from the insertion opening portion 58a to a base point A as it gradually becomes narrower in width, and is formed into a flat surface that extends with a fixed width from the base point A toward the proximal end direction (hereinafter, a portion from the base point A to the inner portion of the insertion hole 58 will be referred to as a measurement hole portion 59).

An interval $I_{mea}$ of the pair of wall portions 62 on the measurement hole portion 59 is set to a value slightly smaller than the thickness $T_{all}$ of the measurement chip 12 in the lamination direction. Accordingly, while the measurement chip 12 is being inserted into the insertion hole 58, the pair of wall portions 62 sandwiches the measurement chip 12 in the left-right width direction and presses the measurement chip 12 inwardly in the lamination direction. In particular, the tip mounting portion 60 formed of a metallic material would have a high rigidity, and dimensions and shapes thereof are molded accurately in the manufacture. Therefore, the interval $I_{mea}$ of the pair of wall portions 62 on the measurement hole portion 59 is set to a predetermined dimensional accuracy with high accuracy, and thus, defines the thickness of the measurement chip 12 inserted between the pair of wall portions 62, with high accuracy and stability.

The tip mounting portion 60 has a pair of element storage spaces 64 in cooperation with the fixing wall 46a of the photometric block 46 in a halfway position where the insertion hole 58 (the measurement hole portion 59) extends. The pair of element storage spaces 64 is a portion of the measurement unit 14, provided at mutually facing positions sandwiching the insertion hole 58. The pair of element storage spaces 64 communicates with the measurement hole portion 59 via each of light guide portions 66 formed by the tip mounting portion 60.

The measurement unit 14 constitutes a light emitting portion 70 by storing a light emitting element 68 in one element storage space 64, and constitutes a light receiving portion 74 by storing a light receiving element 72 in the other element storage space 64. The light guide portion 66 of the tip mounting portion 60 is formed into a circular hole with a suitable diameter, and thus, functions as an aperture.

The light emitting element 68 of the light emitting portion 70 includes a first light emitting element 68a and a second light emitting element 68b. The first light emitting element 68a emits measurement light having a first wavelength onto the measurement chip 12. The second light emitting element 68b emits measurement light having a second wavelength different from the first wavelength, onto the measurement chip 12 (not illustrated in FIG. 2). The first light emitting element 68a and the second light emitting element 68b are arranged in parallel at positions facing the light guide portion 66 of the element storage space 64.

The light emitting elements 68 (the first and second light emitting elements 68a and 68b) can be constituted with light emitting diodes (LED). The first wavelength is a wavelength for detecting color-developing concentration of the reagent 26 according to the amount of blood glucose, that is, for example, 620 nm to 640 nm. The second wavelength is a wavelength for detecting red blood cell concentration in blood, that is, for example, 510 nm to 540 nm. The control unit 42 inside the box portion 44 supplies drive current so as to cause each of the first and second light emitting elements 68a and 68b to emit light at predetermined timing.

The light receiving portion 74 arranges one light receiving element 72 at a position facing the light guide portion 66 of the element storage space 64. The light receiving portion 74 receives transmitted light from the measurement chip 12, and can be configured with a photodiode (PD), for example.

Moreover, the eject pin 56 (eject portion) joined with the eject lever 54 is provided at a bottom portion (proximal end surface) of the insertion hole 58. The eject pin 56 includes a stick portion 56a and a receiving portion 56b. The stick portion 56a extends in the axis direction of the photometric block 46. The receiving portion 56b having a large diameter outwardly in the diameter direction at the distal end portion of the stick portion 56a. The proximal end side 24b of the measurement chip 12 inserted into the insertion hole 58 comes in contact with the receiving portion 56b. Moreover, a coil spring 76 that encloses the eject pin 56 in a non-contact state is provided between the bottom portion of the insertion hole 58 and the receiving portion 56b of the eject pin 56. The coil spring 76 elastically supports the receiving portion 56b of the eject pin 56.

The eject pin 56 is displaced in the proximal end direction when the receiving portion 56b is pressed with insertion of the measurement chip 12 by a user, and locked (fixed) by a locking mechanism (not illustrated) provided inside the housing 40. The coil spring 76 elastically contracts according to the displacement of the receiving portion 56b. When the eject pin 56 slightly moves by operation of the eject lever 54 by the user, the locking of the locking mechanism is released, eject pin 56 slides in the distal end direction by an elastic restoring force of the coil spring 76. With this operation, the measurement chip 12 is pushed by the eject pin 56 and taken out from the insertion hole 58.

Returning to FIG. 1, the control unit 42 of the apparatus main body 16 includes a control circuit having a calculation unit, a storage unit, and an input/output unit (not illustrated). A known computer can be employed as the control unit 42. The control unit 42 detects and calculates glucose in the blood, for example, by performing driving control of the measurement unit 14 according to user operation of the operation button 50, and displays a calculated blood glucose level on the display 52.

Fundamental configurations of the measurement chip 12 and the apparatus main body 16 on the blood glucose meter 10 are as described above. Next the relationship between the dimensions of the measurement chip 12 and the dimensions of the insertion hole 58 on the apparatus main body 16, with action and effects thereof, will be described with reference to FIGS. 3B, 4A to 4C.

As described above, the measurement chip 12 includes a lamination structure in which the pair of plate pieces 30 and the spacer 32 are laminated. Accordingly, the thickness $T_{all}$ of the measurement chip 12 in the lamination direction corresponds to a sum of a plate thickness $T_b$ of the pair of plate pieces 30 and a thickness $T_s$ of the spacer 32. The thickness $T_{all}$ of the measurement chip 12, being in a non-insertion state at the insertion hole 58, would be set to a range of 21 μm to 205 μm, while the thickness $T_s$ of the pair of spacers 32 would be set to a range of 11 μm to 105 μm.

Subsequently, the measurement chip 12 is inserted corresponding to the rectangular shape of the insertion hole 58, such that the short side 24 is fit to the up-down direction of the insertion hole 58, while the thickness in the lamination direction is fitted to the left-right width direction of the insertion hole 58. Meanwhile, the measurement chip 12 has a pair of spacers 32 with a same shape in upper/lower positions, with the cavity 20 positioned at a center in the up-down direction. With this arrangement, the user can insert the measurement chip 12 into the insertion hole 58 without caring about the directions of the right side surface and the left side surface.

Moreover, since the measurement chip 12 is discarded every time after one-time use for measurement, it would be possible to enhance throughput in the manufacture by setting a certain range of allowance for a dimensional error in the product. In particular, while it would be easy to uniformly mold the plate piece 30 with a fixed plate thickness $T_b$, it would be difficult to uniformize the thickness $T_s$ (including thickness of adhesive, or the like) of the spacer 32 joined between the pair of plate pieces 30. Therefore, too much attention paid for achievement of high dimensional accuracy might increase labor and thus increase time taken for mass-production, leading to higher manufacturing cost. In comparison, the measurement chip 12 can significantly suppress the increase in labor and cost for the manufacture by providing allowance for dimensional accuracy in the manufacture.

Meanwhile, the tip mounting portion 60 having the insertion hole 58 is fixed to the apparatus main body 16 that repeats blood glucose measurement. Therefore, the tip mounting portion 60 has the insertion hole 58 that is, for example, molded with highly accuracy using a metallic material so as to be produced with high dimensional accuracy. Among the insertion hole 58, the interval $I_{ent}$ of the pair of wall portions 62 located in the left-right width direction of the insertion opening portion 58a is larger than the thickness $T_{all}$ of the measurement chip 12. Meanwhile, the pair of wall portions 62 gradually becomes slimmer in width along a way from the insertion opening portion 58a toward the base point A, and the interval $I_{mea}$ (width in left-right width direction) of the measurement hole portion 59 on a further inner side of the base point A is smaller than the thickness $T_{all}$ of the measurement chip 12. The interval $I_{mea}$ of the pair of wall portions 62 on the measurement hole portion 59 is set to a range of 20 µm to 200 µm.

With this setting, when the user inserts the measurement chip 12 from the insertion opening portion 58a of the apparatus main body 16 at measurement of a blood glucose level, the measurement chip 12 easily passes through the insertion opening portion 58a. Subsequently, when the measurement chip 12 goes into an inner portion through the insertion opening portion 58a, comes in contact with the pair of wall portions 62 being curved in front of the base point A, and then, the pair of plate pieces 30 is pressed by being guided by the curved surface, leading to elastic contraction of the spacer 32 inwardly in the lamination direction.

Figure 4B:
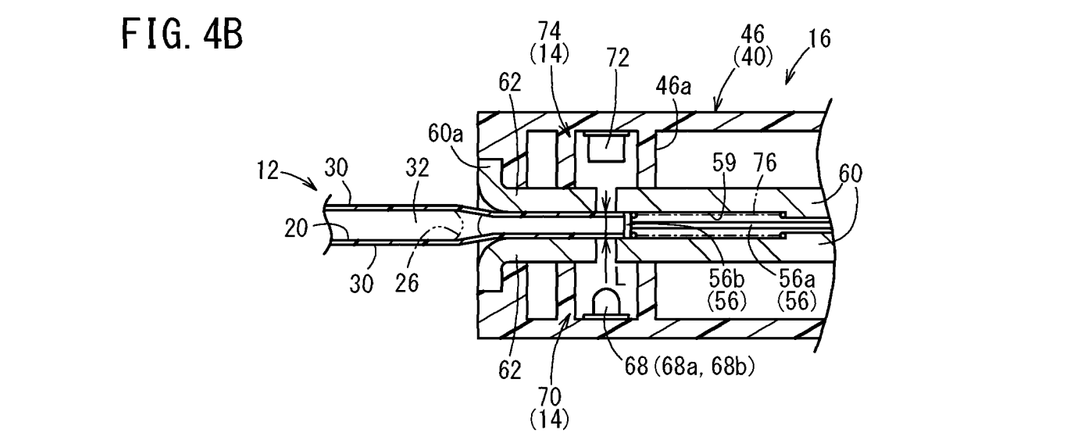
FIG. 4B is a second cross-sectional plan view illustrating attachment operation following the operation in FIG. 4A.

When insertion into the insertion hole 58 continues, the measurement chip 12, receiving friction while being pressed by the pair of wall portions 62, goes into an inner portion of the measurement hole portion 59, as illustrated in FIG. 4B. In other words, among portions of the measurement chip 12, the portion that goes into the measurement hole portion 59 continues to be reduced inwardly in the lamination direction being sandwiched between the pair of wall portions 62. At insertion of the measurement chip 12, the measurement chip 12 comes in contact with the receiving portion 56b of the eject pin 56 at a predetermined position of the insertion hole 58 and presses the eject pin 56 in the proximal end direction.

Figure 4C:
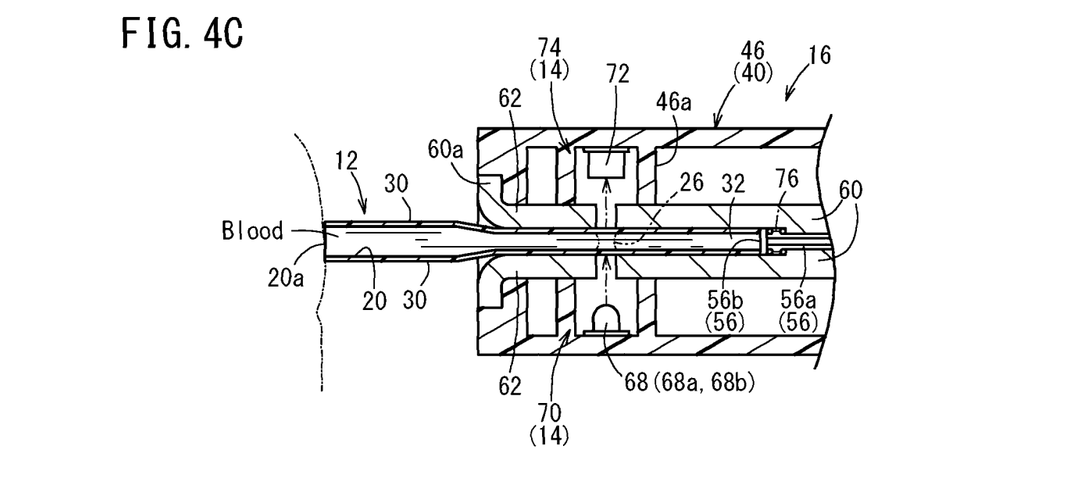
FIG. 4C is a third cross-sectional plan view illustrating attachment operation following the operation in FIG. 4B.

When insertion of the measurement chip 12 is completed, the measurement target portion 28 of the measurement chip 12 is arranged at a position overlapping with the light guide portion 66, as illustrated in FIG. 4C. At this stage, entry of the measurement chip 12 into the inner portion is restricted, while the measurement chip 12 is positioned with a strong friction received from the wall portion 62. Furthermore, the measurement chip 12 allows its thickness $T_{all}$ in the lamination direction to be defined into a fixed dimension by the pair of wall portions 62 of the measurement hole portion 59. In other words, the thickness $T_s$ of the spacer 32 of the measurement chip 12 is constantly uniformized at every measurement.

At this point, using the blood glucose meter 10 that measures a blood glucose level by transmitting the measurement light through the measurement chip 12, the control unit 42 calculates a result of measurement on the basis of Beer-Lambert law indicated in the following formula (1).

$$\log_{10}(I_1/I_0) = -\alpha L \quad (1)$$

In this case, $I_0$ is light intensity before incidence into the blood, $I_1$ is light intensity after emission from the blood, α is absorption coefficient, and L is a distance (herein after, referred to as a cell length) for which the measurement light passes.

Specifically, since the spacer 32 of the measurement chip 12 forms the thickness of the cavity 20, the thickness $T_s$ corresponds to the above-described cell length L (length of a portion in which color-developed blood exists and the measurement light passes through), and affects accuracy in blood glucose measurement. Therefore, the blood glucose meter 10 can be configured such that the pair of wall portions 62 presses the measurement chip 12 inwardly in the lamination direction in a state where the measurement chip 12 is inserted into the measurement hole portion 59, thereby defining the thickness $T_s$ of the spacer 32 (including the measurement target portion 28) positioned in the measurement hole portion 59. As a result, the cell length L of the measurement target portion 28 is constantly achieved at a same level at every measurement (also refer to FIG. 4B). Accordingly, the measurement light emitted from the light emitting portion 70 is transmitted through the measurement chip 12 that constantly achieves a fixed cell length L and received by the light receiving portion 74.

Specifically, the thickness $T_{all}$ of the measurement chip 12 may be set to a level approximately 101% to 105% greater with respect to the interval $I_{mea}$ of the measurement hole portion 59. For example, in a case where the interval $I_{mea}$ of the pair of wall portions 62 is 200 µm, the thickness $T_{all}$ of the measurement chip 12 may be set to 210 µm (plate thickness $T_b$ for each of the pair of plate pieces 30: 50 µm, and thickness $T_s$ for the spacer 32: 105 µm) in a non-insertion state at the measurement hole portion 59. In this case, when the measurement chip 12 is inserted into the measurement hole portion 59, the spacer 32 alone would be elastically deformed, and the thickness $T_{all}$ of the measurement chip 12 is changed to 200 µm (plate thickness $T_b$ for each of the pair of plate pieces 30: 50 µm, and the thickness $T_s$ for the spacer 32: 100 µm). In short, the cell length L of the measurement target portion 28 of the measurement chip 12 is defined to be 100 µm at measurement. In addition, the blood glucose meter 10 can set the cell length L of 100 µm with stability at every measurement even when the thickness $T_{all}$ of the measurement chip 12 is slightly deviated, and thus, it is possible to perform blood glucose measurement with high accuracy.

Note that in a case where the thickness $T_{all}$ of the measurement chip 12 with respect to the interval $I_{mea}$ of the measurement hole portion 59 is larger than 105%, the elastically deformed spacer 32 might narrow the cavity 20 on the inner side to change the volume in the vicinity of the measurement target portion 28 and might affect measurement results. Therefore, by setting the thickness $T_{all}$ of the measurement chip 12 to a range 101% to 105% with respect to the interval $I_{mea}$ of the measurement hole portion 59, it would be possible to smoothly define the cell length L without affecting blood glucose measurement.

As described above, the blood glucose meter 10 and the measurement chip 12 can be configured such that the pair of plate pieces 30 is pressed by the pair of wall portions 62 of the insertion hole 58, and the cell length L (width between the set of plate pieces 30) is defined by elastic deformation of the spacer 32. Accordingly, a fixed thickness (cell length L) of the measurement target portion 28 of the measurement chip 12 is constantly achieved at every blood glucose measurement. With this mechanism, even when the thickness $T_{all}$ includes an error in a non-insertion state at the insertion hole 58, the thickness $T_{all}$ of the measurement chip 12 is favorably changed to a thickness $T_{all}$ defined in an insertion state into the insertion hole 58, making it possible to perform blood glucose measurement with high accuracy and stability. Moreover, it is possible to easily perform mass-production of the measurement chip 12 without the need to pay too much attention to the dimensional accuracy of the measurement chip 12, and thus, to achieve the manufacture with low cost suppressing labor of manufacture.

In this case, by forming the pair of wall portions 62 with a hard material, it is possible to firmly maintain the shape of the insertion hole 58 and to define, with high accuracy, the thickness $T_{all}$ of the measurement chip 12 inserted into the measurement hole portion 59. Furthermore, by arranging the spacers 32 in pair, sandwiching the cavity 20 therebetween, it is possible to uniformly decrease the cell length L with elastic deformation of the pair of spacers 32. This makes it possible to further enhance blood glucose measurement accuracy.

The blood glucose meter 10 and the measurement chip 12 are not limited to the above-described embodiments but may include various modifications and application examples. Hereinafter, some modification examples will be described with reference to FIGS. 5, 6A to 6D.

Figure 5:
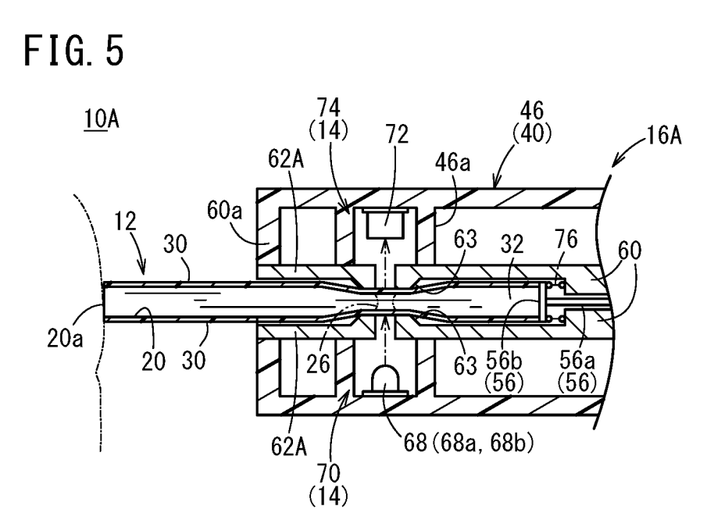
FIG. 5 is a cross-sectional plan view illustrating an enlarged distal end portion of a blood glucose meter according to a first modification example.

As illustrated in FIG. 5, an embodiment of an apparatus main body 16A of a blood glucose meter 10A is configured such that most of an upper portion in the axis direction of the insertion hole 58 is wider than the thickness $T_{all}$ of the measurement chip 12, whereas the portions in the vicinity of the measurement unit 14 are selectively formed to be narrower than the thickness $T_{all}$ of the measurement chip 12. Note that other configurations of the measurement chip 12 and the apparatus main body 16A are same as the configuration of the blood glucose meter 10.

Specifically, the pair of wall portions 62A of the insertion hole 58 includes a pair of raised portions 63, formed with peripheral portions of the light guide portion 66 being raised toward the axis center side of the insertion hole 58. The pair of wall portions 62A constituting portions other than the raised portions 63 of the insertion hole 58 is formed to have an interval wider than the thickness $T_{all}$ of the measurement chip 12, thereby facilitating insertion of the measurement chip 12. In contrast, the interval of the pair of raised portions 63 is the same as the interval $I_{mea}$ of the above-described measurement hole portion 59. The measurement chip 12 is configured to have a fixed cell length L when the measurement target portion 28 and its peripheral portions are pressed inwardly in the lamination direction by the pair of raised portions 63 in an insertion state into the insertion hole 58. Therefore, with the blood glucose meter 10A, it is possible to perform blood glucose measurement with high accuracy and stability, similarly to the blood glucose meter 10.

Figure 6A:
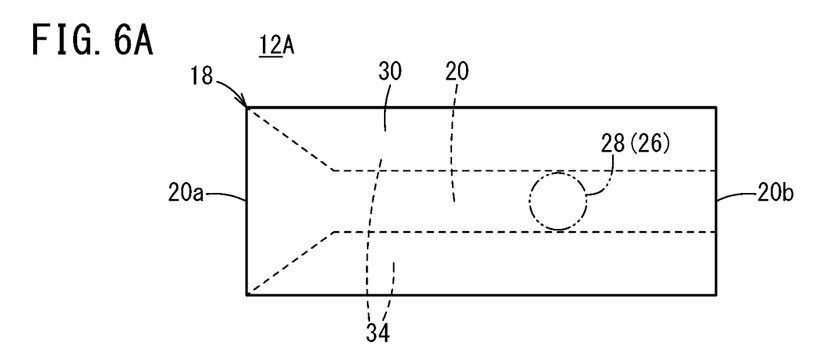
FIG. 6A is a side view illustrating a measurement chip according to a second modification example.

As illustrated in FIG. 6A, another example of a measurement chip 12A is formed in a tapered shape, in a side view, in which a pair of spacers 34 is separating from each other from a predetermined position toward a distal end direction to form a wide width. With this form, it is possible to smoothly take in the blood from the distal end port 20a of the measurement chip 12A, to the cavity 20. In addition, the user can easily recognize the directions of the distal end and proximal end of the measurement chip 12A by checking the tapered state of the measurement chip 12A.

Figure 6B:
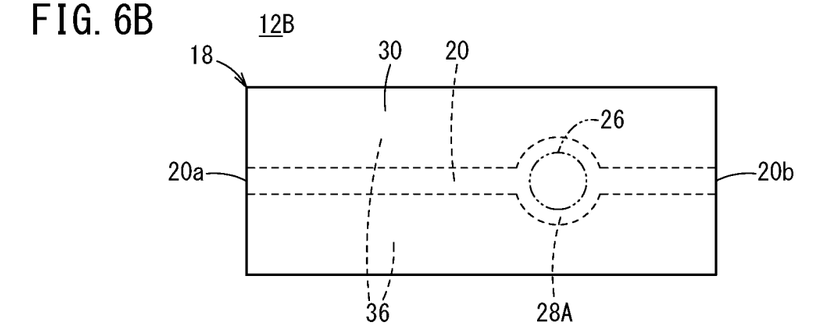
FIG. 6B is a side view illustrating a measurement chip according to a third modification example.

As illustrated in FIG. 6B, still another example of a measurement chip 12B can be configured such that a passage portion of the cavity 20 is formed in a narrow width by using a pair of spacers 36, and the measurement target portion 28A is provided in a large area by cutting out a portion around the application position of the reagent 26 in an arcuate shape. With this arrangement, it is possible to expand a transmission range of the measurement light and increase the light quantity to be detected by the light receiving portion 74, making it possible to enhance accuracy in blood glucose measurement. Additionally, with uniform reduction of the spacers 36 enclosing the measurement target portion 28A, it is possible to define the cell length L of the entire measurement target portion 28A, and thus to further enhance measurement accuracy.

Figure 6C:
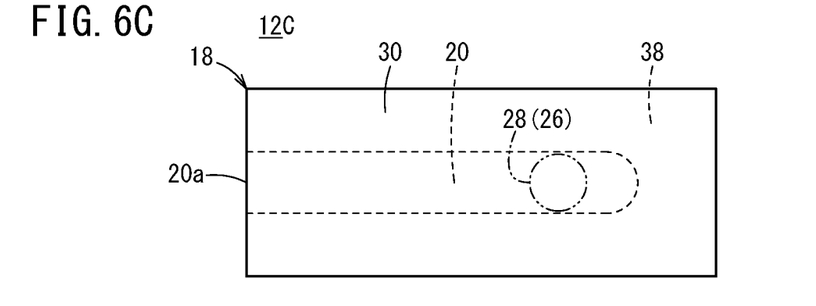
FIG. 6C is a side view illustrating a measurement chip according to a fourth modification example.

As illustrated in FIG. 6C, a measurement chip 12C is configured such that one spacer 38 is formed in a substantially U-shaped and the cavity 20 is provided at an intermediate position of the spacer 38. In this case, the spacer 38 may be formed of a porous material that can cause the gas to flow. In this manner, it is possible to have a same effect even with one spacer 38 provided between the pair of plate pieces 30. In short, the number of spacers arranged between the pair of plate pieces 30 is not particularly limited, but may be three or more, for example.

Figure 6D:
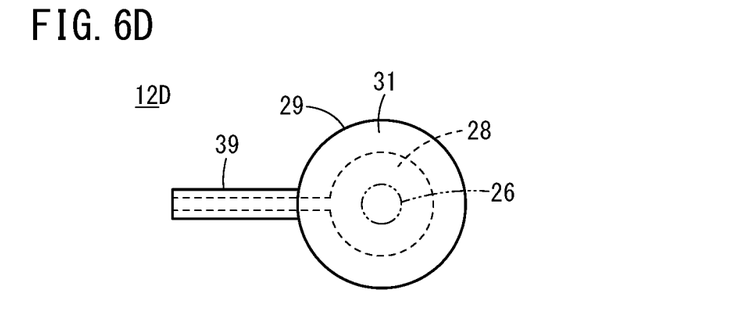
FIG. 6D is a side view illustrating a measurement chip according to a fifth modification example.

As illustrated in FIG. 6D, a measurement chip 12D is configured such that a disc portion 29 is provided to enclose the measurement target portion 28 with a pair of plate pieces 31, and a cylindrical introduction portion 39 for introducing the blood protrudes formed from the disc portion 29. In this manner, the measurement chip 12D having different shapes for the measurement portion (disc portion 29) and the blood introduction portion (introduction portion 39) can also achieve the same effects, even without a rectangular shape in general.

In the above, embodiments regarding the present invention have been described. It should be readily apparent however, that the present invention is not intended to be limited to the above embodiments but various modifications are possible without departing from the scope of the claims. For example, each of the component measurement apparatuses 10 and 10A is not limited to a blood glucose meter but may be applied to various devices for measuring a component included in a liquid. Exemplary component measurement apparatuses 10 and 10A include devices for measuring a component of body fluid such as urine, and devices for measuring a component of industrial water and waste water.

The invention claimed is:

1. A component measurement apparatus comprising:
   a measurement chip, comprising:
   a pair of spacers offset a width distance from one another and extending a length of the measurement chip from a shared proximal end plane to a shared distal end plane, wherein the width distance defines a width of a substantially rectangular liquid-retainable cavity running the length of the measurement chip, and wherein a height of the pair of spacers defines a height of the substantially rectangular liquid-retainable cavity running the length of the measurement chip;
   a first plate piece having an inner surface in contact with each spacer of the pair of spacers on a first side of the measurement chip; and a second plate piece having an inner surface in contact with each spacer of the pair of spacers on an opposite second side of the measurement chip;
wherein the pair of spacers are elastically deformable along the height of the pair of spacers, wherein a total thickness of the measurement chip comprises a thickness of the first plate piece, the height of the pair of spacers, and a thickness of the second plate piece, and wherein the measurement chip has a non-insertion state defining a first dimension for the total thickness of the measurement chip and an insertion state defining a smaller second dimension for the total thickness of the measurement chip; and
an apparatus main body including an insertion hole configured to receive the measurement chip, wherein the insertion hole includes opposing wall portions disposed at a set height distance from one another, and wherein the height distance is smaller than the first dimension for the total thickness of the measurement chip in the non-insertion state;
wherein the component measurement apparatus is configured to measure, by a measurement unit inside the insertion hole, a component of a liquid taken into and retained by the substantially rectangular liquid-retainable cavity of the measurement chip, in a state where the measurement chip is inserted in the insertion hole and is compressed by the opposing wall portions into the insertion state.

2. The component measurement apparatus according to claim 1, wherein the opposing wall portions are formed with a material harder than the first and second plate pieces.

3. The component measurement apparatus according to claim 2, wherein the opposing wall portions are formed from a hard metallic material.

4. The component measurement apparatus according to claim 1, wherein the first and second plate pieces each extend the length of the measurement chip, and wherein the length of the measurement chip is at least two times a total width of the measurement chip.

5. The component measurement apparatus according to claim 1, wherein the total thickness of the measurement chip is set to a range of 101% to 105% of the set height distance between the opposing wall portions, in the non-insertion state at the insertion hole.

6. The component measurement apparatus according to claim 5, wherein the total thickness of the measurement chip is 0.05 mm to 0.5 mm in the non-insertion state.

7. The component measurement apparatus according to claim 6, wherein a predetermined position of the substantially rectangular liquid-retainable cavity along the length of the measurement chip comprises a reagent for developing color on blood.

8. A measurement chip configured to be inserted into an insertion hole of an apparatus main body of a component measurement apparatus, the insertion hole comprising opposing wall portions disposed at a set distance from one another, and configured to allow a component of a liquid that has been taken into and retained by a substantially rectangular liquid-retainable cavity of the measurement chip, to be measured by a measurement unit inside the insertion hole, the measurement chip comprising:
a pair of spacers offset a width distance from one another and extending a length of the measurement chip from a shared proximal end plane to a shared distal end plane, wherein the width distance defines a width of the substantially rectangular liquid-retainable cavity running the length of the measurement chip, wherein a height of the pair of spacers defines a height of the substantially rectangular liquid-retainable cavity running the length of the measurement chip, wherein the liquid-retainable cavity includes a first opening and a second opening, wherein the first opening and the second opening communicate directly with an outside of the measurement chip, and wherein the liquid is taken into the rectangular liquid-retainable cavity of the measurement chip via capillary action through the second opening;
a first plate piece having an inner surface in contact with each spacer of the pair of spacers on a first side of the measurement chip; and
a second plate piece having an inner surface in contact with each spacer of the pair of spacers on an opposite second side of the measurement chip;
wherein the pair of spacers are elastically deformable along the height of the pair of spacers, wherein a total thickness of the measurement chip comprises a thickness of the first plate piece, the height of the pair of spacers, and a thickness of the second plate piece, and wherein the measurement chip has a non-insertion state defining a first dimension for the total thickness of the measurement chip and an insertion state defining a smaller second dimension for the total thickness of the measurement chip.

9. The measurement chip according to claim 8, wherein the pair of spacers are formed from a porous material.

10. The measurement chip according to claim 8, wherein the first and second plate pieces are formed from a thermoplastic material.

11. The measurement chip according to claim 10, wherein the first and second plate pieces each extend the length of the measurement chip, and wherein the length of the measurement chip is at least two times a total width of the measurement chip.

12. The measurement chip according to claim 11, wherein the total width of the measurement chip is 5 mm to 15 mm.

13. The measurement chip according to claim 12, wherein the total thickness of the measurement chip is 0.05 mm to 0.5 mm in the non-insertion state.

14. The measurement chip according to claim 13, wherein at a predetermined position of the substantially rectangular liquid-retainable cavity along the length of the measurement chip, a reagent for developing color on blood is disposed within the substantially rectangular liquid-retainable cavity.

15. The measurement chip according to claim 14, wherein each of the first and second plate pieces is transparent or translucent, and wherein a light transmission path is provided through i) the first plate piece, ii) the substantially rectangular liquid-retainable cavity, and iii) the second plate piece.

16. A method for measuring a characteristic of a bodily fluid using a component measurement apparatus and a measurement chip, comprising:
introducing, prior to inserting the measurement chip into the component measurement apparatus, the bodily fluid into a substantially rectangular liquid-retainable cavity of the measurement chip by capillary action, wherein the bodily fluid is retained in the substantially rectangular liquid-retainable cavity, wherein the measurement chip comprises:
a pair of spacers offset a width distance from one another and extending a length of the measurement chip from a shared proximal end plane to a shared distal end plane, wherein the width distance defines a width of the substantially rectangular liquid-retainable cavity running the length of the measurement chip, and wherein a height of the pair of spacers defines a height of the substantially rectangular liquid-retainable cavity running the length of the measurement chip;
a first plate piece having an inner surface in contact with each spacer of the pair of spacers on a first side of the measurement chip; and
a second plate piece having an inner surface in contact with each spacer of the pair of spacers on an opposite second side of the measurement chip;
wherein the pair of spacers are elastically deformable along the height of the pair of spacers, wherein a total thickness of the measurement chip comprises a thickness of the first plate piece, the height of the pair of spacers, and a thickness of the second plate piece, and wherein the measurement chip has a non-insertion state defining a first dimension for the total thickness of the measurement chip and an insertion state defining a smaller second dimension for the total thickness of the measurement chip;
inserting the measurement chip into an insertion hole of the component measurement apparatus, wherein the component measurement apparatus comprises:
an apparatus main body including the insertion hole configured to receive the measurement chip, wherein the insertion hole includes opposing wall portions disposed at a set height distance from one another, wherein the height distance is smaller than the first dimension for the total thickness of the measurement chip in the non-insertion state, and wherein inserting the measurement chip into the insertion hole, compresses the measurement chip from the non-insertion state to the insertion state, by the opposing wall portions; and
measuring a component of the bodily fluid taken into the substantially rectangular liquid-retainable cavity of the measurement chip by a measurement unit disposed inside the insertion hole.

17. The method according to claim 16, wherein the total thickness of the measurement chip is set to a range of 101% to 105% of the set height distance between the opposing wall portions in the non-insertion state.

18. The method according to claim 17, wherein the total thickness of the measurement chip is 0.05 mm to 0.5 mm in the non-insertion state.

19. The method according to claim 18, wherein a predetermined position of the substantially rectangular liquid-retainable cavity along the length of the measurement chip comprises a reagent for developing color on blood to assist with measuring by the measurement unit.

20. The method according to claim 16, wherein at each of the first and second plate pieces is transparent or translucent, wherein a light transmission path is provided through i) the first plate piece, ii) the substantially rectangular liquid-retainable cavity, and iii) the second plate piece, and wherein measuring the component of the bodily fluid taken into the substantially rectangular liquid-retainable cavity of the measurement chip comprises transmitting measurement light through the measurement chip via the light transmission path.

* * * * *